(12) United States Patent
Takesako et al.

(10) Patent No.: US 6,303,350 B1
(45) Date of Patent: Oct. 16, 2001

(54) PHYSIOLOGICALLY ACTIVE SUBSTANCES TKR2449, PROCESS FOR PRODUCING THE SAME, AND MICROORGANISM

(75) Inventors: Kazutoh Takesako, Otsu; Mitsuhiro Ueno; Naoyuki Awazu, both of Kusatsu; Yoko Uno, Otsu; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/445,543
(22) PCT Filed: Jun. 9, 1998
(86) PCT No.: PCT/JP98/02530
 § 371 Date: Mar. 7, 2000
 § 102(e) Date: Mar. 7, 2000
(87) PCT Pub. No.: WO98/56755
 PCT Pub. Date: Dec. 17, 1998

(30) Foreign Application Priority Data

Jun. 9, 1997 (JP) .................................................. 9-168011

(51) Int. Cl.⁷ ............................ C12P 13/02; C07C 233/00
(52) U.S. Cl. .......................... 435/129; 564/161; 564/167; 564/169; 435/911
(58) Field of Search .................................. 564/161, 167, 564/169; 435/129

(56) References Cited

FOREIGN PATENT DOCUMENTS

| 0 526 936 A2 | 2/1993 | (EP) . |
| WO 94/18157 | 8/1994 | (WO) . |
| WO 97/01275 | 1/1997 | (WO) . |

OTHER PUBLICATIONS

Aureobasidium sp. SN–115, Journal of Fermentation Technology, Japanese Ed., vol. 66, No. 4, pp. 217–223.

Zajic et al, Flocculant and Chemical Properties of a Polysaccharide from *Pullularia pullulans*, Applied Microbiology, Apr. 1973, pp. 628–635.

Schmidtchen et al, Utility of the Cleavage of Nitrosamides for the Preparation of Chiral Acids after Chromatographic Separation of their Diastereomeric Amides, Zeitschrift fuer Naturforschung Section B, vol. 32, No. 1, 1977, pp. 98–104.

*Primary Examiner*—Herbert J. Lilling
(74) *Attorney, Agent, or Firm*—Connolly Bove Lodge & Hutz

(57) ABSTRACT

The present invention has for its object to provide novel biologically active substances which is of value as a therapeutic agent for fungal infections and immune disorders. This invention is related to a biologically active substance TKR2449 analog(s) which is represented by the following general formula (A);

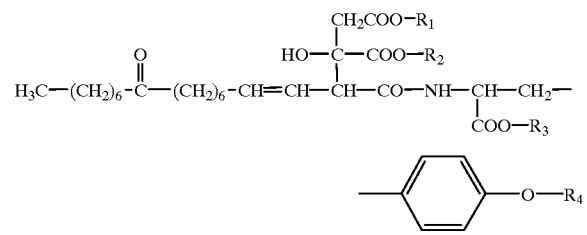

(In the formula, $R_1$, $R_2$ and $R_3$ are the same or differ each other, and each represents hydrogen or an alkyl group of carbon number of 1 to 4. $R_4$ is a linear or branched alkyl or alkenyl group of carbon number of 1 to 8.).

3 Claims, 5 Drawing Sheets

PHYSIOLOGICALLY ACTIVE SUBSTANCES TKR2449, PROCESS FOR PRODUCING THE SAME, AND MICROORGANISM

This application is a 371 of PCT/JP98/02530, Jun. 9, 1998.

TECHNICAL FIELD

The present invention relates to biologically active substances TKR2449 analog(s), which are useful for a therapeutic agent for fungal infection diseases and immune disorders, a method for their production, and microorganisms being capable of producing the biologically active substances TKR2449.

BACKGROUND ART

Fungi are known to cause a variety of infectious diseases in man, animals, and plants. In man, for instance, they cause superficial mycosis affecting the skin, oral cavity, etc. and systemic mycosis affecting the viscera, brain, etc. They cause similar infections in pet and domestic animals as well. Furthermore, fungi inflict various hazardous effects on plants such as orchard trees and vegetables.

As the principal pathogenic fungi causing systemic mycosis in man, those of the genera Candida, Cryptococcus, and Aspergillus, among others, are known. As to superficial mycosis, genus Candida affecting the skin, oral cavity, and vagina and trichophytons infecting the skin of the extremities are regarded as the major pathogenic fungi. Besides those fungi, many other fungi exist in the environment and are suspected to contaminate the animals and plants.

Recently allergic disorders including asthma, atopic dermatitis, and allergic rhinitis are rapidly increasing. There are lots of allergic disorders in which various substances in the environment such as mites and all kinds of pollen, or antigens contained in foods actas allergens. Also there are many allergic disorders caused by fungi, and allergens derived from Candida, Aspergillus, Alternaria, Cladosporium, Malassezia, Penicillium, etc. act as their causes. Further, lots of immune disorders other than allergic disorders, in which immune responses are exacerbated are known.

As antimycotics of use for the prevention and treatment of such fungal infections and contaminations, only a very few are known nowadays. Among them, as therapeutic drugs for systemic mycosis in animals especially including men, for instance, amphotericin B, flucytosine, miconazole, and fluconazole can be mentioned. However, those compounds are not fully satisfactory in potency, toxic potential, or antifungal spectrum, thus being not impeccable as therapeutic drugs.

Although there are lots of therapeutics for immune disorders including allergic diseases, they cannot treat a variety of immune disorders sufficiently. In particular, there is only a few drugs that have plural good functions like activity to control immune disorders and antifungal activity.

SUMMARY OF THE INVENTION

In view of the above-mentioned prior art, the present invention has for its object to provide novel biologically active substances which are of value as a therapeutic agent for fungal infections and immune disorders.

In the search for a novel biologically active substance, the inventors isolated a large number of microorganisms from the natural kingdom, isolated the biologically active substances they produced, and scrutinized their biological properties. As a result, they discovered that the culture broth of a strain of microorganism belonging to the genus Aureobasidium contains a biologically active substance having antifungal activity against pathogenic fungi inclusive of *Candida albicans* and *Cryptococcus neoformans*. Accordingly, the inventors isolated this biologically active substance and studied its physicochemical properties. As a result, they discovered that the above substance is a novel substance having distinct physicochemical characteristics and not having mentioned in the literatures, and they named it TKR2449. Furthermore, they discovered that TKR2449 shows a biologically active effect on an immune system and completed the present invention.

The present invention, therefore, is directed to a biologically active substance TKR2449 analog(s) which is represented by the following general formula (A);

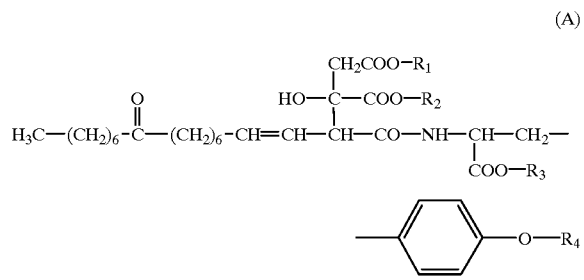

(In the formula, $R_1$, $R_2$ and $R_3$ are the same or differ each other, and each represents hydrogen or an alkyl group of carbon number of 1 to 4. $R_4$ is a linear or branched alkyl or alkenyl group of carbon number of 1 to 8.)

The present invention is further directed to a method of preparing the biologically active substance TKR2449 which comprises culturing a strain of microorganism belonging to the genus Aureobasidium and being capable of producing the biologically active substance TKR2449, and isolating the objective substance from the resulting culture broth.

In addition, the present invention is directed to a microorganism belonging to the genus Aureobasidium and being capable of producing the biologically active substance TKR2449.

DETAILED DESCRIPTION OF THE INVENTION

The present invention is related to the biologically active substances TKR2449 analog(s) represented by the general formula (A) described above.

In the general formula (A) described above, $R_1$, $R_2$ and $R_3$ are the same or differ each other, and each represents a hydrogen or an alkyl group having the carbon number of 1 to 4. The alkyl group having the carbon number of 1 to 4 is not limited but includes methyl, ethyl, propyl, n-butyl, and i-butyl groups. Preferably, $R_1$, $R_2$ and $R_3$ are hydrogen.

In the general formula (A) described above, $R_4$ is a linear or branched alkyl or alkenyl group having the carbon number of 1 to 8. The linear or branched alkyl group having the carbon number of 1 to 8 is not limited but includes methyl, ethyl, propyl, n-butyl, and i-butyl groups. The linear or branched alkenyl group having the carbon number of 1 to 8 is not limited but includes vinyl, and allyl group. Preferably, $R_4$ is —$CH_2$—CH=C—($CH_3$)$_2$.

In the general formula (A) mentioned above, the substance which has hydrogen as $R_1$, $R_2$ and $R_3$, and —$CH_2$—CH=C—($CH_3$)$_2$ as $R_4$ is the biologically active substance TKR2449 represented by the following formula (I).

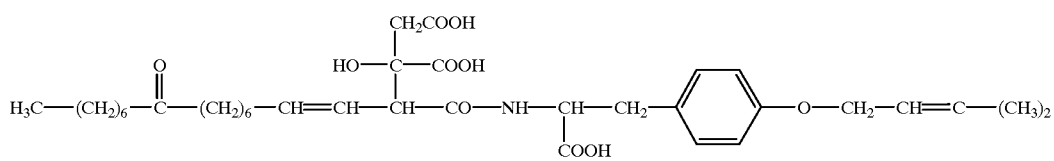

(I)

The biologically active substance TKR2449 described above has the following physicochemical characteristics (1), (2), (3), (4) and (5).
(1) Mass spectrum by FAB-MS gives a peak at m/z 660 [M+H]$^+$
(2) The carbon number is 36 and the nitrogen number is one.
(3) UV spectrum in methanol shows that major absorption wavelengths (nm) are 226 nm and 277 nm, and their $E^{1\ \%}_{1\ cm}$ are 73 and 10, respectively.
(4) IR spectrum by KBr method shows that major wavelength numbers are 3420 cm$^{-1}$, 2930 cm$^{-1}$, 2850 cm$^{-1}$, 1720 cm$^{-1}$, 1510 cm$^{-1}$, 1380 cm$^{-1}$, 1240 cm$^{-1}$, 1200 cm$^{-1}$, 1140 cm$^{-1}$, 1070 cm$^{-1}$, 840 cm$^{-1}$ and 720 cm$^{-1}$.
(5) Soluble in methanol and chloroform, and slightly soluble in water and hexane.

Figure 3:
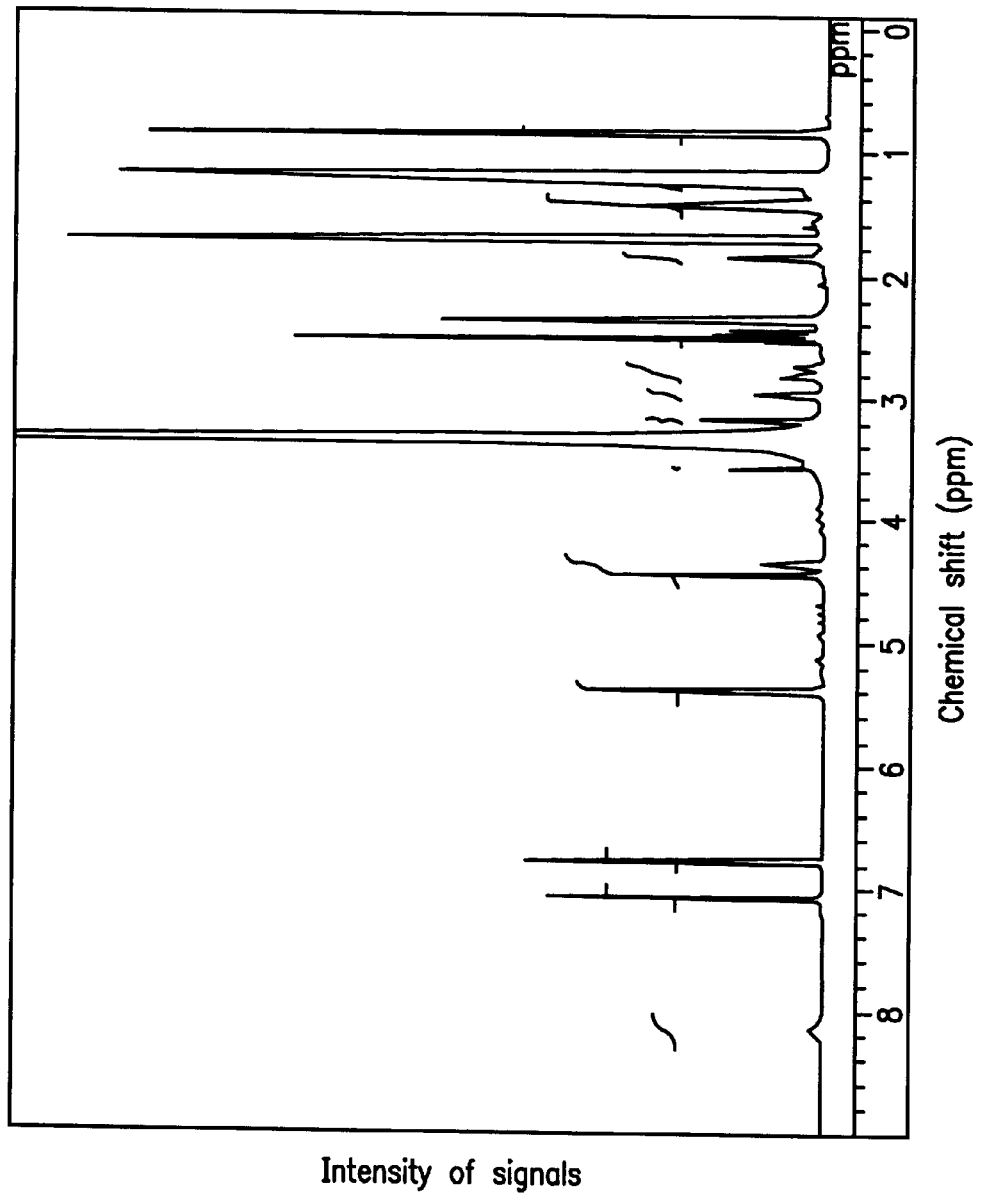
FIG. 3 is a chart showing the $^1$H-NMR spectrum of the biologically active substance TKR2449, in which the ordinate represents intensity of signals and the abscissa represents chemical shift (ppm).
Figure 4:
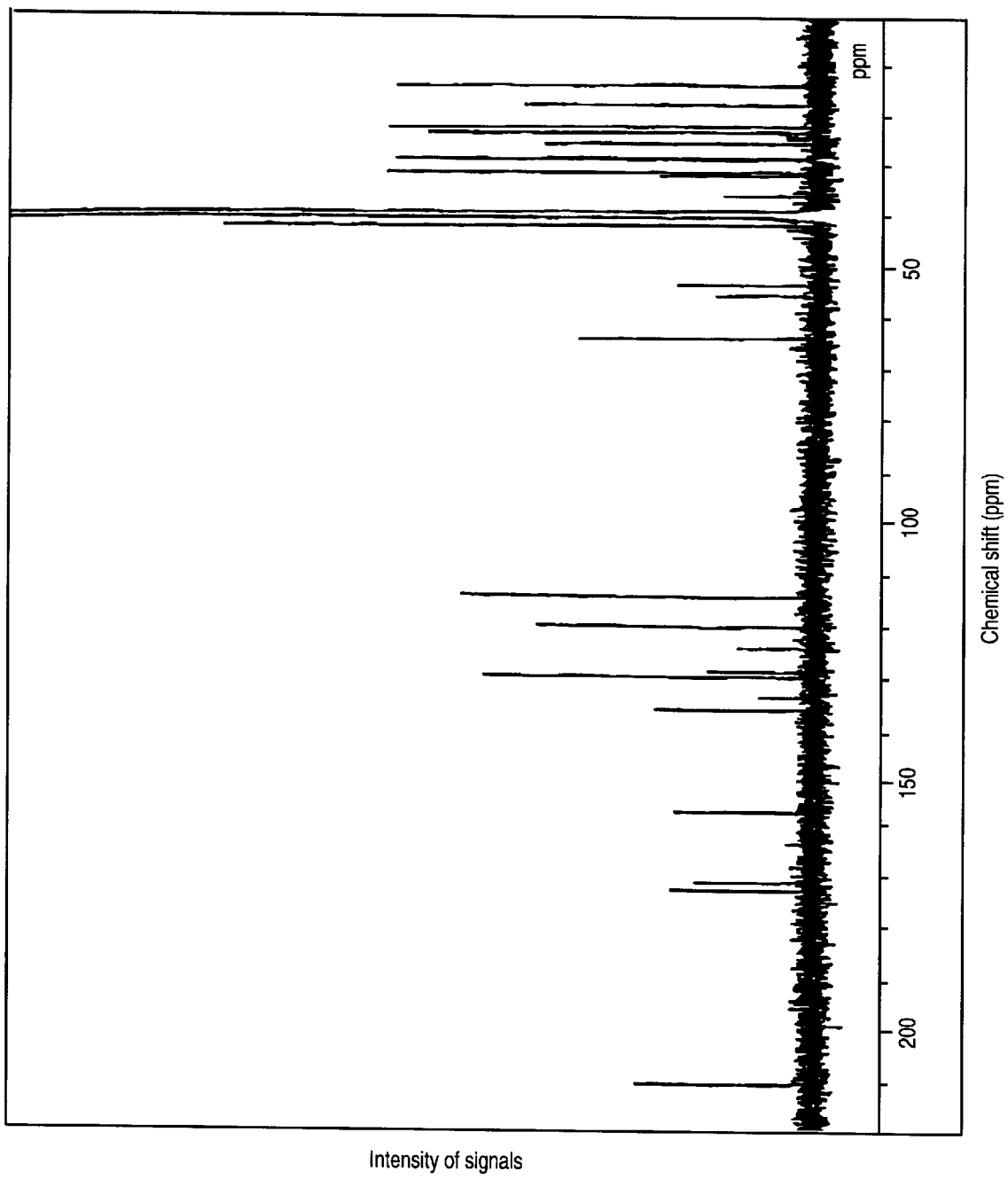
FIG. 4 is a chart showing the $^{13}$C-NMR spectrum of the biologically active substance TKR2449, in which the ordinate represents intensity of signals and the abscissa represents chemical shift (ppm).
Figure 5:
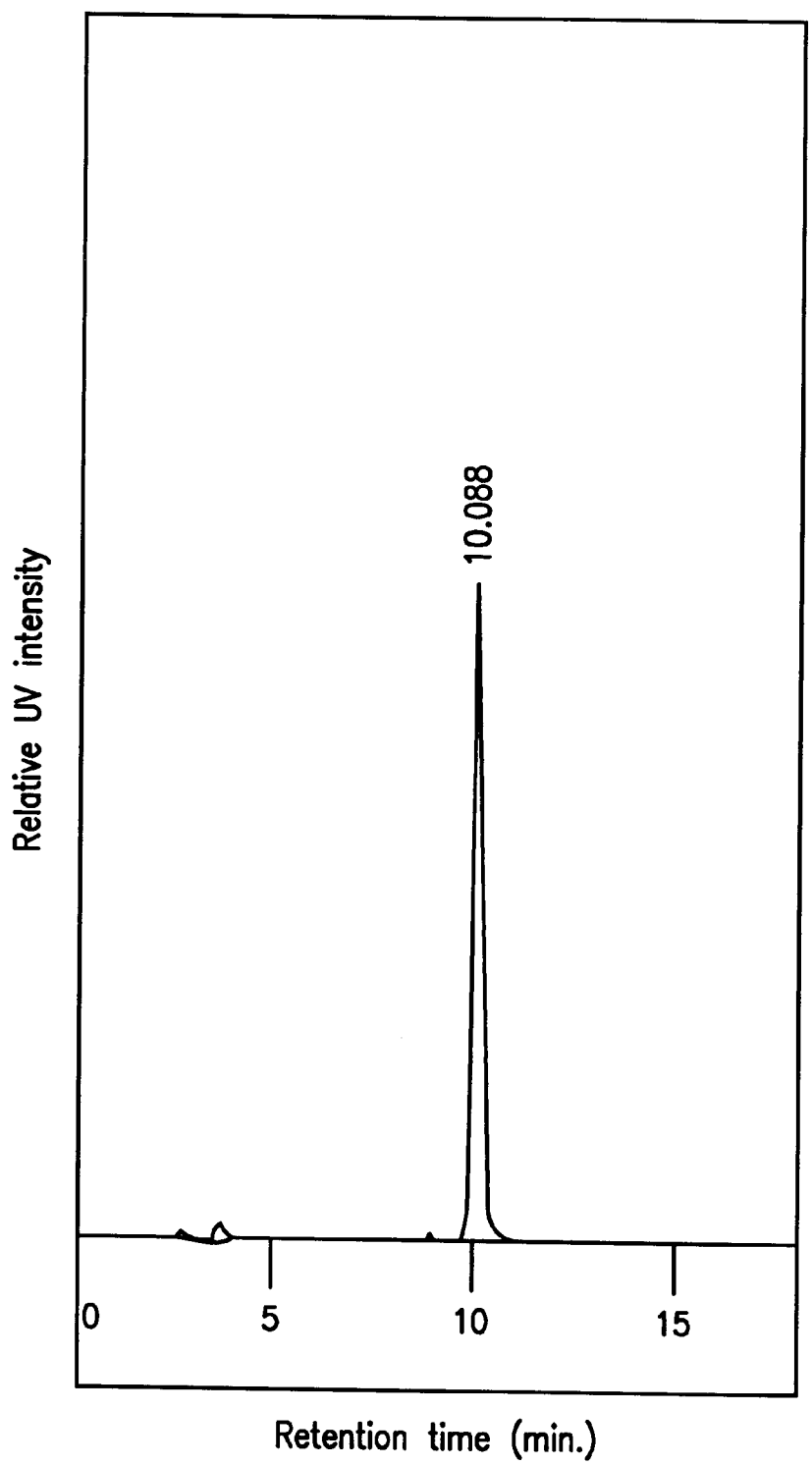
FIG. 5 is a HPLC chart of the biologically active substance TKR2449 showing its elution position, in which the ordinate represents relative UV intensity and the abscissa represents retention time (min.).

The biologically active substance TKR2449 mentioned above has the $^1$H-NMR spectrum shown in FIG. 3 and the $^{13}$C-NMR spectrum shown in FIG. 4 and the characteristics such that it is eluted at the position indicated in FIG. 5 in the reversed-phase high-performance liquid chromatography.

The above-mentioned biologically active substance TKR2449 can be prepared by culturing a strain of microorganism belonging to the genus Aureobasidium and being capable of producing said biologically active substance TKR2449, and isolating said substance from the resulting culture broth.

In addition, TKR2449 analog(s) represented by the general formula (A) can be obtained from the above-mentioned biologically active substance TKR2449 used as a starting material by the methods described below.

For example, a methylester derivative ($R_1$=$R_2$=$R_3$=$CH_3$) can be obtained by treating the above-mentioned biologically active substance TKR2449 with trimethylsilyl diazomethane (TMSCHN$_2$) in a solvent mixture of benzene and methanol. The corresponding ester derivative ($R_1$=$R_2$=$R_3$=R) can be obtained by reacting it with various alcohols (R—OH) in dimethyl formamide (DMF) in the presence of a condencing agent including dicyclohexyl carbodiimide (DCC).

$R_4$ in the above general formula (A) can be removed by treatment with a hydrogen halide including hydrogen iodide (HI) or with a base including sodium methoxide (CH$_3$ONa), or by treatment with sodium iodide (NaI) and tetrachlorosilane (SICl$_4$) in a solvent mixture of dichloromethane and acetone. After said removal, preparing a methyl ester derivative ($R_1$=$R_2$=$R_3$=$CH_3$), the corresponding ether derivative (—O—$R_4$) can be obtained by reacting with sodium hydride (NaH) and various alkyl halide ($R_4$—X; X=I, Br, Cl) or with various alkyl trichloroacetoimide ester ($R_4$OC(=NH)CCl$_3$). Thereafter, —COOR$_1$, —COOR$_2$ and —COOR$_3$ are removed to obtain free carboxyl groups, for example, by treating with alkali including NaOH in methanol.

There is no limitation on the strain of microorganism that can be used in the present invention only provided it belongs to the genus Aureobasidium and can produce said TKR2449. Thus, for example, Aureobasidium sp. TKR2449 (hereinafter referred to as the strain TKR2449) can be mentioned.

The above-mentioned strain TKR2449 is a novel strain not heretofore described in the literature, and isolated and characterized for the first time by the inventors. The strain has the property to produce TKR2449 with advantage. The mycological characteristics of the above mentioned strain TKR2449 are now described in detail.

The colors of colonies of said strain TKR2449 on various media are shown in Table 1. The descriptions of colors in the table are based on those prescribed in Japanese Industrial Standard (JIS) Z 8102 (1985) and shows the results of observation on days 4, 7 and 14 of culture at 25° C. after inoculation in the respective media. The diameter of the colonies was measured after 14 days culture.

TABLE 1

| Medium | Diameter of colony (mm) | Color of colony (Day 4) | Color of colony (Day 7) | Color of colony (Day 14) |
| --- | --- | --- | --- | --- |
| Malt extract agar | 58 | Pale yellow 2.5Y9/2 | Dark grayish yellow-green 5GY3/2 | Dark grayish yellow-green 5GY3/2 |
| Potato dextrose agar | 49 | Ivory 5Y8/2 | Ivory 5Y8/2 | Ivory 5Y8/2 |
| Sabouraud agar | 64 | Pale yellow 2.5Y9/2 | Pale yellow 2.5Y9/2 | Dark green-gray 5GY3/1 |

TABLE 1-continued

| Medium | Diameter of colony (mm) | Color of colony (Day 4) | Color of colony (Day 7) | Color of colony (Day 14) |
| --- | --- | --- | --- | --- |
| YpSs agar | 38 | Light grayish yellow-red 5YR8/2 | Light grayish yellow-red 5YR8/2 | Light grayish yellow-red 5YR8/2 |

The above strain TKR2449 grows moderately on malt extract agar and YpSs agar, etc. Its colony has glitter in the center, and is generally viscous or pasty, but sometimes becomes leathery as passing the days of culture. Rhizoid-like structures are often formed around the colonies. The color of colonies is white in the beginning of culture, then gradually changing pale yellow to ivory locally, and becomes dark grayish yellow-green to dark green-gray as time goes by. After additional days, the color of colonies becomes brown to dark brown. This pigment is insoluble.

The Hyphae have the diameter of 2 to 3 $\mu$m and elongate with good growth, however they do not form aerial mycelia and elongate into the agar media. Blastic conidia with a size of 3–4×3–8 $\mu$m are often formed like finger tips from head or side of Hyphae and sometimes ball-like clusters are observed. Young vegetative cells look yeast-like, the size is 2–4×5–14 $\mu$m, the shape is ellipsoidal or lemon-like, and they grow by polyblastic budding. Arthrospores with a size of 4–6×8–10 $\mu$m, and chlamydospores with a size of 4–8× 8–16 $\mu$m are formed, and ascospores are not formed.

Among the mycological characters of the strain TKR2449, its physiological characteristics are described as follows.

Temperature range for growth: The temperature range for growth is 10 to 30° C. and the optimum range of temperature for growth is around 25° C.

The pH range for growth: The pH range for growth is pH 3 to 8 and the optimum range of pH for growth is pH 4 to 7.

When the above mycological characters are compared with the descriptions of genus Aureobasidium in W. B. Cooke, Mycopathologia et Mycologia Applicata, 17, 1–43 (1962); J. A. von Arx, The Genera of Fungi Sporulating in Pure Culture, J. Cramer, Lehre; E. J. Hermanides-Nijhoff, Studies inMycology, 15, 141–166, CBS, Baarn (1977); and other literatures, the strain TKR2449 can be identified to be a strain belonging to the genus Aureobasidium.

However, no report has mentioned a strain of microorganism belonging to the genus Aureobasidium and having the ability to produce TKR2449. Therefore, the inventors regarded it as a novel strain and named Auleobasidium sp. TKR2449. The strain was deposited under the Budapest Treaty with National Institute of Bioscience and Human Technology (Address, 1–3, Higashi 1-chome, Tsukuba-shi, Ibaraki, Japan (Zip code 305-8566)) under the accession number of FERM BP-6327 (original date of deposit: Jun. 4, 1997; date of request for transfer to international deposit: Apr. 20, 1998).

The present invention can be carried into practice not only with the above-mentioned strain TKR2449 but also with any spontaneous or artificial mutant of said strain TKR2449 or any other strain of microorganism belonging to the genus Aureobasidium and having the ability to produce TKR2449.

In accordance with the present invention, TKR2449 is prepared by inoculating and cultivating a TKR2449-producing strain in a nutrient medium. Nutrients to be used for the medium include various carbon sources such as glucose, fructose, saccharose, starch, dextrin, glycerol, molasses, thick malt syrup, oils and fats, and organic acids. Those materials can be used independently or in a suitable combination thereof.

Nutrients to be used for the medium include nitrogen sources organic and inorganic nitrogen compounds such as soybean meal, cotton seed meal, corn steep liquor, casein, peptone, yeast extract, meat extract, wheat germs, urea, amino acids, ammonium salts, etc. Salts as nutrients are various inorganic salts such as salts of sodium, potassium, calcium, magnesium, phosphoric acid, etc. Those materials can be used independently or in a suitable combination thereof.

Where necessary, the nutrient medium may be supplemented with heavymetal salts such as iron salts, copper salts, zinc salts, cobalt salts, etc., vitamins such as biotin, vitamin $B_1$, etc., and other organic and inorganic substances which would assist in growth of the microorganism and promote production of TKR2449.

In addition to the above nutrients, an antifoamer and/or a surfactant, for example silicone oil, polyalkylene glycol ethers, etc., can be added to the nutrient medium mentioned above.

In cultivating a strain of microorganism being capable of producing TKR2449 in said nutrient medium, a variety of methods which are generally used in the production of biologically active substances by culturing microorganisms can be employed. Among them, liquid culture, particularly shake culture or submerged aerobic culture, is preferred.

The cultivation is preferably carried out at a temperature of 15 to 25° C. The pH of the medium may range from pH 3 to 8 and is preferably around pH 5. Regarding the incubation time, generally a sufficient output of the substance can be expected by 3 to 15 days of culture.

By the above-mentioned cultivation, TKR2449 is contained both intracellularly and extracellularly and accumulated in the culture broth. In the present invention, the TKR2449 accumulated in the culture broth can be obtained from the broth by isolation utilizing its physicochemical characteristics and, where necessary, further purification.

The above-mentioned isolation can be achieved by extracting the whole broth with a non-hydrophilic organic solvent such as ethyl acetate, butyl acetate, chloroform, butanol, methyl isobutyl ketone or the like. As an alternative, it is possible to subject the broth to centrifugation or filtration to separate into the medium and cells and isolate the biologically active substances from each of the medium and cells.

The TKR2449 can be isolated from the separated medium not only by the extraction method using the above-mentioned non-hydrophilic organic solvent but also by the method which comprises contacting the medium with an adsorbent to let TKR2449 adsorbed on the adsorbent and eluting them with a solvent. The adsorbent includes, for example, activated carbon, cellulose powder and adsorbent resins. As the above-mentioned solvent, a variety of solvents can be selectively used according to the kind and properties of the adsorbent and either singly or in combination. Thus, suitable combination of an aqueous solution of water-soluble organic solvents such as aqueous acetone, aqueous alcohol, etc. can be employed.

For isolation of TKR2449 from the separated microorganisms, the extraction technique using a hydrophilic organic solvent such as acetone can be employed.

In the present invention, where necessary, the crude extract of TKR2449 can be followed by the purification process. Said purification can be curried out with the methods generally used for the isolation and purification of fat-soluble biologically active substances. As such methods, there can be mentioned column chromatography or high-performance liquid chromatography using a column packed with a stationary phase such as silica gel, activated alumina, activated charcoal, adsorbent resin, etc. The eluent that can be used for silica gel column chromatography includes chloroform, ethyl acetate, methanol, acetone, water, etc. They can be used in a combination of two or more kinds thereof.

The resin for high-performance liquid chromatography includes chemically-derivatized silica gel such as silica gel derivatives having octadecyl, octyl or phenyl groups; and polystyrenic porous polymer gels, while the mobile phase that can be used includes aqueous solutions of water-soluble organic solvents such as aqueous methanol, aqueous acetonitrile, etc.

TKR2449 analog(s) of the present invention can each be put to use as such or in the form of a pharmacologically acceptable salt in medicinal applications. There is no particular limitation on said salt provided that it is a pharmacologically acceptable salt. Thus, the salt includes salts of mineral acids such as hydrochloric acid, sulfuric acid, nitric acid, phosphoric acid, hydrofluoricacid, hydrobromic acid, etc.; saltsoforganic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc.; and salts of alkali metals or alkaline earth metals such as sodium, potassium, calcium, etc.

To administer TKR2449 analog(s) or its pharmacologically acceptable salt as a drug, TKR2449 analog(s) or its pharmacologically acceptable salt can be administered either as such or in the form of a pharmaceutical composition containing typically 0.1 to 99.5%, preferably 0.5 to 90% thereof in a pharmaceutically acceptable, non toxic and inert carrier to animals inclusive of humans.

The carrier mentioned above includes solid, semisolid or liquid diluents, fillers, other formulation auxiliaries, etc. and such carriers can be used alone or in combination.

The above-mentioned pharmaceutical composition is preferably administered in unit dosage forms and can be administered orally, parenterally, topically (e.g. transdermally) or rectally. Of course, those pharmaceutical compositions should be administered in dosage forms suited for the respective route of administration.

For administration of TKR2449 analog(s) of the present invention or its pharmacologically acceptable salt as a drug, the dose as an antifungal agent is preferably selected with reference to patient factors such as age and body weight, route of administration, nature and severity of disease, etc. Usually in man, however, the daily dose of the active ingredient for an adult patient is 10 to 2000 mg. While a daily dose lower than the above range maybe sufficient in some cases, a dose higher than the range may be required in other cases. When a high dose is used, the daily dosage is preferably administered in several divided doses.

The oral administration can be made using solid, powdery, or liquid unit dosage forms and, for example, bulc powders, powders, tablets, dragees, capsules, drops, sublingual tablets and other dosage forms can be used.

For the parenteral administration, liquid unit dosage forms for subcutaneous, intramuscular or intravenous administration, typically solutions and suspensions, can be employed. These preparations can be manufactured by suspending or dissolving a predetermined amount of TKR2449 analog(s) of the present invention or a pharmaceutically acceptable salt thereof in a nontoxic liquid carrier suitable for injection such as an aqueous medium or an oily medium, and sterilizing the resulting suspension or solution.

The topical administration (e.g. transdermal administration) can be carried out using a topical dosage forms such as liquids, creams, powders, pastes, gels and ointments. These dosage forms can be manufactured by using a predetermined amount of TKR2449 analog(s) or a pharmacologically acceptable salt thereof in combination with one or more of the perfume, coloring agent, filler, surfactant, humectant, emollient, gelatinizer, carrier, preservative, stabilizer, etc. suitable for external dosage formulations.

The rectal administration mentioned above can be made using, for example, suppositories each mixing a predetermined amount of TKR2449 analog(s) or its pharmacologically acceptable salt with a low-melting solid base such as higher esters, e.g. myristyl palpitate, polyethylene glycol, cacao butter or a mixture of them.

BEST MODE OF CARRYING OUT THE INVENTION

The following examples are further illustrative of the present invention, but by no means limitative of the scope of the invention.

EXAMPLE 1

A loopful of strain TKR2449 (FERM BP-6327) from a slant culture was used to inoculate into a 500-ml Erlenmeyer flask containing 100 ml of liquid medium (Difco potato dextrose broth, 2.4% (w/v)) and incubated on a shaker at 25° C. for 3 days to prepare a seed culture. This seed culture 1.0 ml was. transferred to 8 Erlenmeyer flasks of 500 ml capacity each containing 125 ml of the same liquid medium as above and incubated (under shaking at 220 rpm) at 25° C. for 12 days. The obtained culture broth was centrifuged and the supernatant was separated from cells. The supernatant was applied to a column (0.5 L) of Diaion HP20 (Mitsubishi Chemical Co. Ltd.), the column was washed with water, and eluted with 2 L of 80% methanol to give an active fraction. The fraction was concentrated under reduced pressure to obtain 205 mg of a residue.

The residue was dissolved in 0.8 ml of methanol and subjected to high-performance liquid chromatography to provide an active fraction. The fraction was concentrated under reduced pressure to obtain 6.8 mg as a white powder. The high-performance liquid chromatography was carried out under the following conditions.

Apparatus: LC-8A (Shimadzu)

Column: YMCPack C18 (2.0 cm×25 cm) (YMC)

Mobile phase: 70% (v/v) of acetonitrile/water containing 0.05% trifluoroacetic acid Physicochemical Properties Mass spectrometry was carried out by JMS-DX302 mass spectrometer (Jeol Ltd.). $^1$H-NMR (in deuterated methanol, with tetramethylsilane as reference) and $^{13}$C-NMR (in deuterated methanol, with deuterated methanol as reference) were performed by JNM-A500 nuclear magnetic resonance spectrometer (Jeol Ltd.). Ultraviolet spectrophotometry (in methanol) was carried out by UV-250 self-recording spectrophotometer (Shimadzu), and infrared absorption spectrometry (KBr method) was by 270-30 infrared spectrophotometer (Hitachi). Physicochemical properties of the substance TKR2449 are described below.

(1) Mass Spectrometry

The purified white powdery product available upon vacuum concentration of the active fraction in said high-performance liquid chromatography was found to be a substance with m/z 660 [M+H]+ by FAB-MS mass spectrometry.

(2) Numbers of Carbons and Nitrogens

The purified white powdery product available upon vacuum concentration of the active fraction in said high-performance liquid chromatography was found that the carbon number is 36 and the nitrogen number is 1 by $^1$H-NMR, $^{13}$C-NMR and their analyses. The $^1$H-NMR spectrum and $^{13}$C-NMR spectrum of this product are shown in FIG. 3 and FIG. 4, respectively.

(3) Ultraviolet Absorption Spectrum

The UV absorption in methanol of the purified white powdery product available upon vacuum concentration of the active fraction in the high-performance liquid chromatography was found to be as follows.

UV (nm) ($E^1{}_1{}^%{}_{cm}$): 226 (73), 277 (10)

Figure 1:
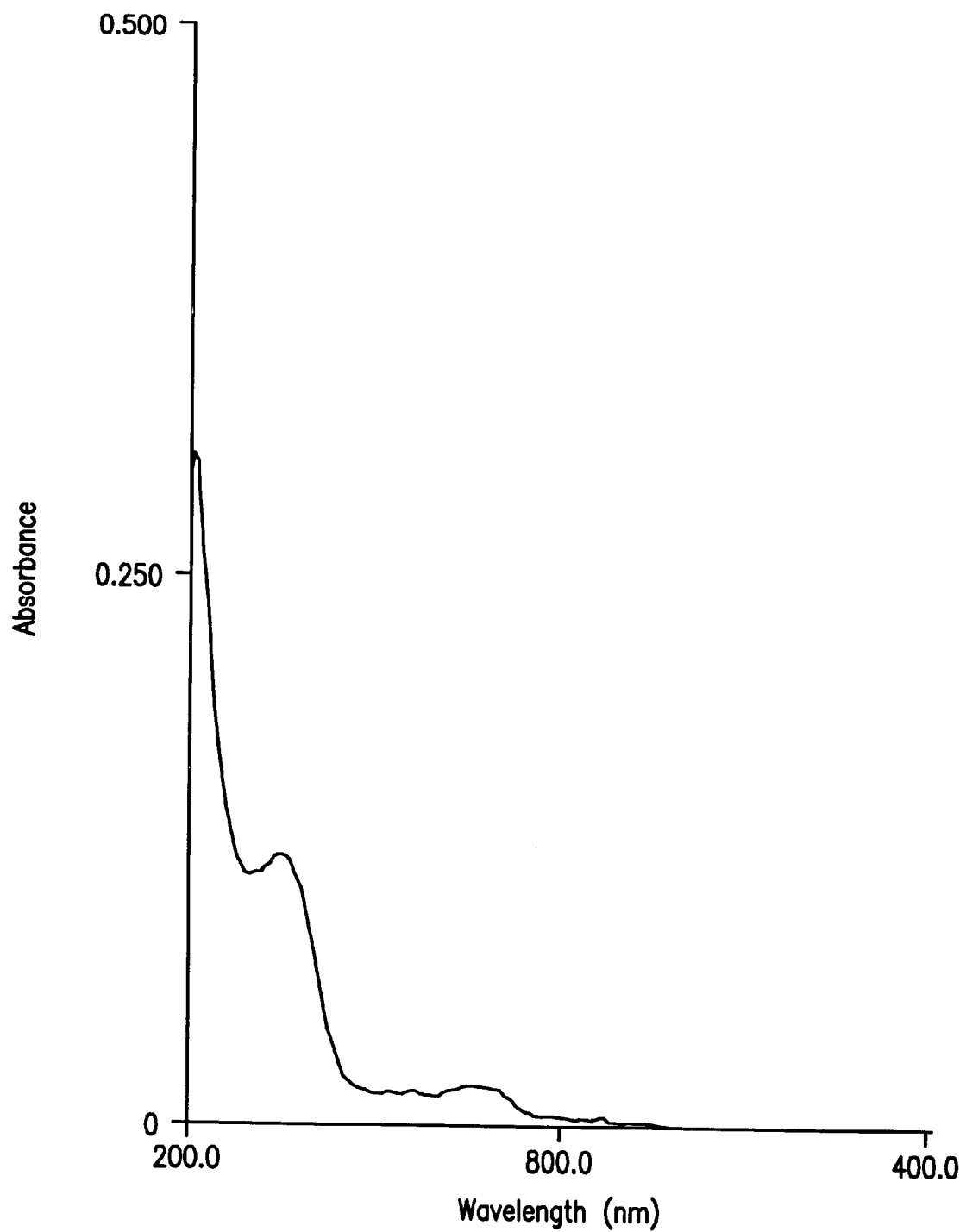
FIG. 1 is a chart showing the ultraviolet absorption spectrum of the biologically active substance TKR2449, in which the ordinate represents absorbance and the abscissa represents wavelength (nm).

The UV absorption spectrum is shown in FIG. 1.

(4) Infrared Absorption Spectrum

The result of IR absorption spectrophotometry by KBr method of the purified white powdery product available upon vacuum concentration of the active fraction in the high-performance liquid chromatography were mentioned in the following.

IR (KBr) (cm$^{-1}$): 3420, 2930, 2850, 1720, 1510, 1380, 1240, 1200, 1140, 1070, 840, 720.

Figure 2:
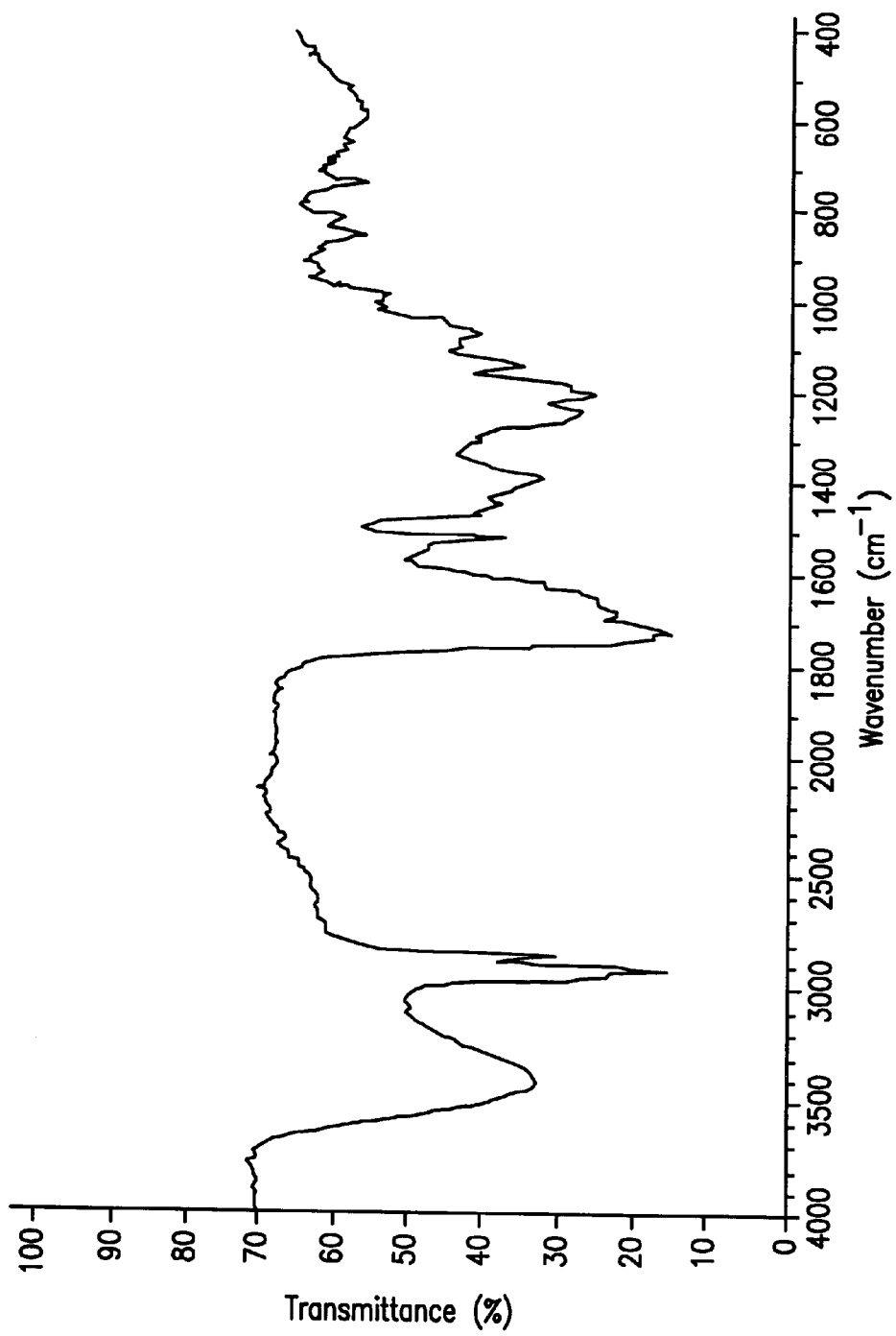
FIG. 2 is a chart showing the infrared absorption spectrum of the biologically active substance TKR2449, in which the ordinate represents transmittance (%) the abscissa represents wavenumber ($cm^{-1}$).

The IR absorption spectrum is shown in FIG. 2.

As for the solubility of the obtained TKR2449 in various solvents, it was soluble in methanol and chloroform, but slightly soluble in hexane and water.

Based on the above analyses, the purified white powdery product available upon vacuum concentration of the active fraction in the high-performance liquid chromatography was identified to be TKR2449.

The above TKR2449 was analyzed by reversed-phase partition high-performance liquid chromatography (HPLC) using LC-10A high-performance liquid chromatography (Shimadzu). This HPLC analysis was carried out under the following conditions.

Column: CAPCELL PAK $C_{18}$ (6 mm×150 mm) (Shiseido)

Mobile phase: 70% (v/v) of acetonitrile/water containing 0.05% trifluoroacetic acid Column temperature: 40° C.

Detection UV wavelength: 220 nm

As a result, the above TKR2449 was eluted in the position indicated in FIG. 5.

Biological Characteristics (1) Antifungal Activity

The antifungal spectra of the above TKR2449 against various microorganisms were determined. Using the liquid medium dilution method, the concentration causing substantially complete inhibition of fungal growth was determined as the minimal inhibitory concentration (μg/ml). The results are shown in Table 2. The minimal concentration causing partial inhibition of fungal growth was determined as the sub-inhibitory concentration (μg/ml) and are shown in parentheses in Table 2.

In the table, YNBG stands for a YNBG medium comprising 0.67% of yeast nitrogen base (Difco) and 1.0% of glucose.

TABLE 2

| Test strain | Medium | Minimal inhibitory concentration (μg/ml) |
|---|---|---|
| Candida albicans TIMM0136 | YNBG | 12.5 (6.25) |
| Candida kefyr TIMM0301 | YNBG | 100 (25) |
| Cryptococcus neoformans TIMM0354 | YNBG | 6.25 |

It is apparent from Table 2 that the biologically active substance TKR2449 according to the present invention is active against pathogenic fungi such as Candida albicans, Candida kefyr, Cryptococcus neoformans etc.

(2) Inhibitory Activity of Mixed Lymphocytes Reaction (MLR)

Spleens of C57BL/6 mice and BALB/c mice were respectively taken, and homogenized in a medium to be a cell suspension. The cell suspension from C57BL/6 mice was passed through a nylon wool column, yielding a T cell-rich preparation (responder cells). The cell suspension from BALB/c mice was irradiated by X ray and used as stimulator cells. The responder cells and the stimulator cells were mixed at a ration of 1:1, and incubated in a $CO_2$ incubator. After incubation for 4 days, $^3$H-thymidine was added. After incubation for additional one day, the cells were harvested. The amount of $^3$H-thymidine incorporated was measured. Test samples, which were prepared by dilution of a solution in dimethylsulfoxide to be solutions of 500, 125, 31.2 and 7.8 μg/ml with culture medium, were added by 0.5% when responder cells and stimulator cells were mixed, and the final concentrations were 2.5 to 0.039 μg/ml. The inhibitory activity was calculated compared to the amount incorporated without a test sample. TKR2449 showed a dose-dependent inhibitory activity of MLR and the concentration showing 50% inhibition was 0.15 μg/ml, showing that it has inhibitory effect for the immune response.

Intraperitoneal administration of the TKR2449 obtained above at a dose of 50 mg/kg to ICR mice caused no toxic signs.

EXAMPLE 2

Preparation of a Methylated TKR2449 ($R_1=R_2=R_3=CH_3$)

TKR2449 (5.0 mg, 7.6 μmol) was dissolved in methanol-benzene (2:8, 50 μl). To the solution, trimethyl diazomethane (10% solution in hexane, 50 μl, 44 μmol) was added at room temperature. The reaction mixture was stirred for 2.5 hours and 10% acetic acid was added to it until it turned clear to decompose trimethyl diazomethane. Thereafter, the mixture was concentrated under reduced pressure. The residue obtained was dissolved in 400 μl of methanol and applied to high performance liquid chromatography. The fraction containing the methylated TKR2449 was concentrated under reduced pressure, yielding 1.9 mg of a purified substance as white powder. The high-performance liquid chromatography was carried out under the following conditions.

Apparatus: LC-8A (Shimadzu)

Column: CAPCELL PAK $C_{18}$ (10 mm×250 mm) (Shiseido)

Mobile phase: 70% (v/v) of acetonitrile/water containing 0.05% trifluoroacetic acid FAB-MS: m/z 701 [M+H]+

INDUSTRIAL APPLICABILITY

The present invention provides the biologically active substances TKR2449 analog(s) which are of use in clinical medicine, for example in the therapy of fungal infectious diseases or immue diseases, and a method for production thereof.

What is claimed is:

1. A biologically active substance TKR2449 analog which is represented by the following general formula (A);

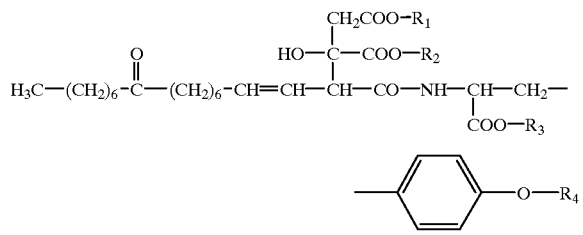

(In the formula, $R_1$, $R_2$ and $R_3$ are the same or differ each other, and each represents hydrogen or an alkyl group of carbon number of 1 to 4, $R_4$ is a linear or branched alkyl or alkenyl group of carbon number of 1 to 8).

2. The biologically active substance TKR2449 analog according to claim 1, having a hydrogen as $R_1$, $R_2$ and $R_3$, and —$CH_2$—CH=C—$(CH_3)_2$ as $R_4$.

3. A method for preparing the biologically active substance TKR2449 which comprises culturing a strain of microorganism belonging to the genus Aureobasidium and being capable of producing the biologically active substance TKR2449, and isolating the objective substance from the resulting culture broth.

* * * * *